United States Patent
Ohtani et al.

(10) Patent No.: US 12,403,112 B2
(45) Date of Patent: Sep. 2, 2025

(54) AGENT FOR PREVENTING, AMELIORATING, OR TREATING PERIODONTAL DISEASE

(71) Applicant: WAKUNAGA PHARMACEUTICAL CO., LTD., Osaka (JP)

(72) Inventors: Masahiro Ohtani, Akitakata (JP); Tsubasa Nishimura, Akitakata (JP)

(73) Assignee: WAKUNAGA PHARMACEUTICAL CO., LTD., Osaka (JP)

( * ) Notice: Subject to any disclaimer, the term of this patent is extended or adjusted under 35 U.S.C. 154(b) by 900 days.

(21) Appl. No.: 17/610,973

(22) PCT Filed: May 13, 2020

(86) PCT No.: PCT/JP2020/019096
§ 371 (c)(1),
(2) Date: Nov. 12, 2021

(87) PCT Pub. No.: WO2020/230813
PCT Pub. Date: Nov. 19, 2020

(65) Prior Publication Data
US 2022/0273597 A1    Sep. 1, 2022

(30) Foreign Application Priority Data
May 14, 2019   (JP) ................... 2019-091444

(51) Int. Cl.
*A61K 31/198*    (2006.01)
*A61P 1/02*    (2006.01)

(52) U.S. Cl.
CPC .............. *A61K 31/198* (2013.01); *A61P 1/02* (2018.01)

(58) Field of Classification Search
CPC ............................. A61K 31/198; A61P 1/02
See application file for complete search history.

(56) References Cited

U.S. PATENT DOCUMENTS

| | | | |
|---|---|---|---|
| 10,238,616 B2 * | 3/2019 | Suzuki | A61P 43/00 |
| 10,363,234 B2 * | 7/2019 | Ushijima | A23L 33/105 |
| 11,717,502 B2 * | 8/2023 | Ushijima | A61K 36/8962 514/561 |
| 2012/0189710 A1 | 7/2012 | Steggles | |
| 2014/0050677 A1 | 2/2014 | Ott | |

(Continued)

FOREIGN PATENT DOCUMENTS

| | | |
|---|---|---|
| JP | 62-423 A | 1/1987 |
| JP | 2004-123630 A | 4/2004 |

(Continued)

OTHER PUBLICATIONS

Bakri et al., Arch Oral Biol, 2004, 50:645-651 (Year: 2004).*

(Continued)

*Primary Examiner* — Andrew D Kosar
*Assistant Examiner* — Jonathan D Mahlum
(74) *Attorney, Agent, or Firm* — Oblon, McClelland, Maier & Neustadt, L.L.P.

(57) ABSTRACT

Provided is a medicine or food useful for preventing, ameliorating or treating periodontal disease. An agent for preventing, ameliorating or treating periodontal disease comprises one or more cysteine derivatives selected from the group consisting of S1PC, SAC and SAMC or a salt thereof as an active ingredient.

4 Claims, 3 Drawing Sheets (Mean±SD, *$P<0.05$ in comparison to control (0 μM), n=3-4)

(56) References Cited

U.S. PATENT DOCUMENTS

| | | |
|---|---|---|
| 2017/0071839 A1 | 3/2017 | Ott |
| 2017/0360731 A1 | 12/2017 | Suzuki et al. |
| 2018/0147170 A1 | 5/2018 | Ushijima et al. |
| 2020/0147021 A1 | 5/2020 | Ushijima et al. |

FOREIGN PATENT DOCUMENTS

| | | |
|---|---|---|
| WO | WO 2011/012855 A2 | 2/2011 |
| WO | WO 2011/037411 A2 | 3/2011 |
| WO | WO 2016/088892 A1 | 6/2016 |
| WO | WO 2016/199885 A1 | 12/2016 |
| WO | WO 2018/182399 A1 | 10/2018 |
| WO | WO 2019/031442 A1 | 2/2019 |
| WO | 109692143 A | 4/2019 |

OTHER PUBLICATIONS

Colin-Gonzalez et al., Oxid Med Cell Longev, 2012, 1-16 (Year: 2012).*
Lawson et al., J Agric Food Chem, 2005, 53:6254-6261 (Year: 2005).*
Rassoul et al., Phytomedicine, 2006, 13:230-235 (Year: 2006).*
Bayan et al., Avicenna J Phytomed, 2014, 4:1-14 (Year: 2014).*
Ushijima et al., J Pharm Pharmacol, 2018, 70:559-565 (Year: 2018).*
Beklen et al., J Dent Res, 2007, 86:347-351 (Year: 2007).*
Xiao et al., Eur J Nutr, 2013, 52:179-191 (Year: 2013).*
Suzuki et al., Sci Rep, 2018, 8:14148 (Year: 2018).*
Nibali et al., Dimens Den Hyg, 2013, 11:28, 30, 32-34 (Year: 2013).*
International Search Report issued on Jul. 21, 2020 in PCT/JP2020/019096 filed May 13, 2020, 3 pages.
Zini, A., et al., "The Efficacy of Aged Garlic Extract on Gingivitis—A Randomized Clinical Trial", Journal of Clinical Dentistry, vol. XXIX, No. 2, 2018, pp. 52-26.
Sojod, B., et al., "RANK/RANKL/OPG Signalization Implication in Periodontitis: New Evidence from A Rank Transgenic Mouse Model", Frontiers in Physiology, vol. 8, Article 338, 2017, pp. 1-12.
Van Kilsdonk, J., et al., "The Effects of Human Beta-Defensins on Skin Cells in vitro", Dermatology, vol. 233, 2017, pp. 155-163.
Hans, M., et al., "Epithelial Antimicrobial Peptides: Guardian of the Oral Cavity", International Journal of Peptides, vol. 2014, ID 370297, 2014, pp. 1-13.
Ebrahem, M., "Expression of human beta defensins (HBDs) 1, 2 and 3 in gingival crevicular fluid of patients affected by localized aggressive periodontitis", The Saudi Dental Journal, vol. 25, 2015, pp. 75-82.
Cui, D., et al., "Human β-defensin 3 inhibits periodontitis development by suppressing inflammatory responses in macrophages", Molecular Immunology, vol. 91, 2017, pp. 65-74.
Yan, L., et al., "Critical Role of Tumor Necrosis Factor Signaling in Mesenchymal Stem Cell-Based Therapy for Autoimmune and Inflammatory Diseases", Frontiers in Immunology, vol. 9, Article 1658, 2018, pp. 1-13.
Li, S., et al., "microRNA-142 is upregulated by tumor necrosis factor-alpha and triggers apoptosis in human gingival epithelial cells by repressing BACH2 expression", American Journal of Translational Research, vol. 9, No. 1, 2017, pp. 175-183.
Lawson, C., et al., "ICAM-1 signaling in endothelial cells", Pharmacological Reports, vol. 61, 2009, pp. 22-32.
Lyck, R., et al., "The physiological roles of ICAM-1 and ICAM-2 in neutrophil migration into tissues", Current Opinion in Hematology, vol. 22, No. 1, 2015, pp. 53-59.
Wang, L., et al., "Evaluation of ICAM-1 and VCAM-1 Gene Polymorphisms in Patients with Periodontal Disease", Medical Science Monitor, vol. 22, 2016, pp. 2386-2391.
"Ninniku no Kagaku (in Japanese, The Science of Garlic)", 1st Ed., 2000, pp. 93-122 (with Partial Translation).
Lv, Y., et al., "Anti-cancer activities of S-allylmercaptocysteine from aged garlic", Chinese Journal of Natural Medicines, vol. 17, No. 1, 2019, pp. 43-49.
Tsuneyoshi, T., et al., "S-1-Propenylcysteine augments BACH1 degradation and heme oxygenase 1 expression in a nitric oxide-dependent manner in endothelial cells", Nitric Oxide, vol. 84, 2019, pp. 22-29.
Kyo, E., "cancer prevention effect of garlic", Journal of Clinical and experimental medicine, vol. 204, No. 1, 2003, pp. 74-79, 7 total pages (with Partial Translation).
Extended European Search Report issued Dec. 16, 2022 in European Patent Application No. 20804962.7, 7 pages.
Kodera et al., Chemistry of aged garlic: Diversity of constituents in aged garlic extract and their production mechanisms via the combination of chemical and enzymatic reactions (Review), Experimental and Therapeutic Medicine, 19, 1574-1584 (2020) (11 pages).
Matsutomo et al., Development of an Analytic Method for Sulfur Compounds in Aged Garlic Extract with the Use of a Postcolumn High Performance Liquid Chromatography Method with Sulfur-Specific Detection, The Journal of Nutrition, 2016 (6 pages).
Ignacio Jiménez-Amezcua et al., A Comparative Study of LC-MS and FIA-(ESI) MS for Quantitation of S-Allyl-L-Cysteine in Aged Garlic Supplements, Foods 2024, 13, 2645 (13 pages).
Hiroko Taguchi et al., Effect of LPS Inoculation into Rat Gingivalis on IL-6 and TNF-α Production—Analysis Using In vivo microdialysis, with a partial English translation (Abstract) of Nihon Univ Dent J, 89, 63-70, 2015 (9 pages).
Masahiro Ohtani et al., Sulfur-containing amino acids in aged garlic extract inhibit inflammation in human gingival epithelial cells by suppressing intercellular adhesion molecule-1 expression and IL-6 secretion, Biomedical Reports 12: 99-108, 2020 (10 pages).

* cited by examiner (Mean ± SD, **$P<0.01$ in comparison to control (0 μM) and #$P<0.05$ in comparison to TNF-α alone, n=4)

AGENT FOR PREVENTING, AMELIORATING, OR TREATING PERIODONTAL DISEASE

TECHNICAL FIELD

The present invention relates to an agent for preventing, ameliorating, or treating periodontal disease.

BACKGROUND ART

Gingivitis is an inflammatory disease in which an inflammatory reaction occurs in the gingiva, triggered by an immune response to the contact and invasion, into gingival cells, of periodontal bacteria in a biofilm, such as a highly malignant *Porphyromonas gingivalis* that induces periodontal disease (collectively meaning gingivitis and periodontitis) (Non Patent Literature 1). In addition, gingivitis shifts to the chronic inflammatory condition due to persistence and prolongation of the inflammatory reaction by leaving it untreated without physical treatment such as removal of biofilm. Chronic inflammation leads to gingival recession and resorption of alveolar bone supporting the roots of teeth by accelerating the degradation of collagen fibers in gingival tissues due to matrix metalloproteinase (MMP) activation and by promoting osteoclast differentiation via an increased expression of receptor activator of NF-κB ligand (RANKL) molecules in osteoblasts, which eventually leads to tooth loss (periodontitis) (Non Patent Literature 1, 2).

Systemic epithelial cells, by producing and releasing antimicrobial substances such as antimicrobial peptides, cooperate with immune cells to act as barriers to prevent the invasion of various microorganisms into a living body, and are also involved in the regulation of innate immune responses (Non Patent Literature 3). Gingival epithelial cells also contribute to the elimination of periodontal bacteria by releasing bactericidal substances such as an antibacterial peptide (Non Patent Literature 4). In the oral cavity, various types of antimicrobial peptides such as defensins, cathelicidin, adrenomedullin, calprotectin and histatin have been identified (Non Patent Literature 4). It has been reported that, among these, typical antimicrobial peptides in humans include defensin and LL-37 produced from cathelicidin (precursors); however, human beta difensin-1,3 (hBD1,3) mRNA in a gingival crevicular exudate is present at a low level in patients with gingivitis or periodontitis (Non Patent Literature 5). It is known that Kostmann syndrome, which is congenital agranulocytosis, is an inherited disease in which the amount of LL-37 produced is extremely low, and the prevalence of periodontal disease is high (Non Patent Literature 4). Furthermore, it has been reported that in experimental models of periodontal disease, direct administration of hBD3 to the peritoneal cavity or into the periodontal pockets inhibits resorption of alveolar bone (Non Patent Literature 6). Thus, it is thought that the antimicrobial peptide plays an important role not only in the prevention of systemic infections but also in the prevention of periodontal disease, and substances that promote the production and release of antimicrobial peptides may inhibit (prevent) the onset of periodontal disease.

Tumor necrosis factor-α (TNF-α), a pro-inflammatory cytokine, exhibits various biological activities such as survival, proliferation, and differentiation of immune cells via the linking to receptors (TNFR1/2) (Non Patent Literature 7). In periodontal pathology, TNF-α is released from macrophages and neutrophils infiltrating the gingival tissue, and excessively accumulated, thereby promoting the production and release of IL-6 in the gingival cells (Non Patent Literature 8). The released IL-6 increases the expression levels of RANKL, promotes osteoclast differentiation, and aggravates periodontal disease (Non Patent Literature 8).

Intercellular adhesion molecule-1 (ICAM-1) is a type of cell-cell adhesion factors, which is expressed on the cell surfaces of leukocytes, endothelial cells, epithelial cells, etc. by inflammatory stimuli, and is involved in adhesion between immune cells or between epithelial or endothelial cells and immune cells (Non Patent Literature 9, 10). Therefore, the persistent expression of ICAM-1 promotes the retention of immune cells at the inflammatory site and causes the prolongation of the inflammatory reaction, resulting in the aggravation of the inflammatory disease such as periodontal disease (Non Patent Literature 11).

Therefore, in chronic periodontal disease, drugs that down-regulate the expression of ICAM-1 and the reduce release of IL-6 in gingival cells may alleviate or treat periodontal disease.

Meanwhile, S-allylcysteine (hereinafter abbreviated as "SAC"), S-1-propenylcysteine (hereinafter abbreviated as "S1PC"), and S-allylmercaptocysteine (hereinafter abbreviated as "SAMC") are water-soluble compounds produced by enzymatic reaction when cutting, crushing, grating, or aging *Allium* plants such as garlic. (Non-Patent Literature 12).

It has been reported that SAC has many pharmacological effects such as a preventive effect on hepatopathy (Patent Literature 1), and SAMC has also an anticancer effect and apoptosis-inducing effect (Non Patent Literature 13).

It has been reported that S1PC has a hypotensive effect (Patent Literature 2) and an effect of promoting the expression of antioxidant enzyme (Non Patent Literature 14).

However, it has not been reported that S1PC, SAC and SAMC have an effect of promoting the expression of antimicrobial peptides in the gingiva or inhibiting gingival inflammation.

CITATION LIST

Patent Literature

Patent Literature 1: JP 05-060447 B
Patent Literature 2: WO 2016/199885 A

Non Patent Literature

Non Patent Literature 1: Zini A, Mann J, Mazor S, Vered Y. The Efficacy of Aged Garlic Extract on Gingivitis—A Randomized Clinical Trial. Journal of Clinical Dentistry 29: 52-56 (2018).
Non Patent Literature 2: Sojod B, Chateau D, Mueller C G, Babajko S, Berdal A, Lezot F, Castaneda B. RANK/RANKL/OPG signalization implication in periodontitis: New evidence from a RANK transgenic mouse model. Frontiers in Physiology 8: 338 (2017).
Non Patent Literature 3: van Kilsdonk Patrick J W J, Jansen P A M, van den Bogaard E H, Bos C, Bergers M, Zeeuwen P L J M, Schalkwijk J. The effects of human beta-defensins onskin cells in vitro. Dermatology 233: 155-163 (2017).
Non Patent Literature 4: Hans M, Hans V M. Epithelial antimicrobial peptides: Guardian of the oral cavity. International Journal of Peptides 2014: ID370297 (2014).
Non Patent Literature 5: Ebrahem M A. Expression of human beta defensins (HBDs) 1, 2 and 3 in gingival crevicular fluid of patients affected by localized aggressive periodontitis. The Saudi Dental Journal 25: 75- (2013).

Non Patent Literature 6: Cui D, Lyu J, Li H, Lei L, Bian T, Li L, Yan F. Human b-defensin 3 inhibits periodontitis development by suppressing inflammatory responses in macrophages. Molecular Immunology 91: 65-74 (2017).

Non Patent Literature 7: Yan L, Zheng D, Xu R H. Critical role of tumor necrosis factor signaling in mesenchymal stem cell-based therapy for autoimmune and inflammatory diseases. Frontiers in Immunology 9: 1658 (2018).

Non Patent Literature 8: Li S, Song Z, Dong J, Shu R. MicroRNA-142 is upregulated by tumor necrosis factor-alpha and triggers apoptosis in human gingival epithelial cells by repressing BACH2 expression. American Journal of Translational Research 9: 175-183 (2017).

Non Patent Literature 9: Lawson C, Wolf S. ICAM-1 signaling in endothelial cells. Pharmacological Reports 61: 22-32 (2009).

Non Patent Literature 10: Lyck R, Enzmann G. The physiological roles of ICAM-1 and ICAM-2 in neutrophil migration into tissues. Current Opinion in Hematology 22: 53-59 (2015)

Non Patent Literature 11: Wang L, Li X H, Ning W C. Evaluation of ICAM-1 and VCAM-1 Gene Polymorphisms in Patients with Periodontal Disease. Medical Science Monitor 22: 2386-2391 (2016).

Non Patent Literature 12: "Ninniku no Kagaku (in Japanese, The Science of Garlic)", 1st Ed., p. 93-122, 2000

Non Patent Literature 13: Liu Y, So K F, Wong N K, Xiao J. Anti-cancer activities of S-allylmercaptocysteine from aged garlic. Chinese Journal of Natural Medicine 17: 43-39 (2019).

Non Patent Literature 14: Tsuneyoshi T, Kunimura K, Morihara N. S-1-Propenylcysteine augments BACH1 degradation and heme oxygenase 1 expression in a nitric oxide-dependent manner in endothelial cells. Nitric Oxide 84: 22-29 (2019).

SUMMARY OF INVENTION

Technical Problem

The present invention relates to provision of a medicine or food useful for preventing, ameliorating, or treating periodontal disease.

Solution to Problem

The present inventors found that a specific cysteine derivative selected from S1PC, SAC and SAMC has an effect of promoting the expression of antimicrobial peptide and an anti-inflammatory effect in human gingival epithelial cells, and these are useful as an agent for preventing or treating periodontal disease.

That is, the present invention relates to 1) to 12) below.

1) An agent for preventing, ameliorating or treating periodontal disease, comprising one or more cysteine derivatives selected from the group consisting of S1PC, SAC and SAMC or a salt thereof as an active ingredient.

2) The agent for preventing, ameliorating or treating periodontal disease according to 1), which promotes expression of antimicrobial peptide in gingiva.

3) The agent for preventing, ameliorating or treating periodontal disease according to 1) or 2), wherein gingival inflammation is inhibited by down-regulating expression of ICAM-1 and/or reducing release of IL-6.

4) An agent for promoting expression of antimicrobial peptide in gingiva, comprising one or more cysteine derivatives selected from the group consisting of S-1-propenylcysteine, S-allylcysteine and S-allylmercaptocysteine or a salt thereof as an active ingredient.

5) Food for preventing or ameliorating periodontal disease, comprising one or more cysteine derivatives selected from the group consisting of S-1-propenylcysteine, S-allylcysteine and S-allylmercaptocysteine or a salt thereof as an active ingredient.

6) Food for promoting expression of antimicrobial peptide in gingiva, comprising one or more cysteine derivatives selected from the group consisting of S-1-propenylcysteine, S-allylcysteine and S-allylmercaptocysteine or a salt thereof as an active ingredient.

7) Use of one or more cysteine derivatives selected from the group consisting of S-1-propenylcysteine, S-allylcysteine and S-allylmercaptocysteine or a salt thereof for producing an agent for preventing, ameliorating or treating periodontal disease.

8) Use of one or more cysteine derivatives selected from the group consisting of S-1-propenylcysteine, S-allylcysteine and S-allylmercaptocysteine for producing an agent for promoting expression of antimicrobial peptide in gingiva.

9) One or more cysteine derivatives selected from the group consisting of S-1-propenylcysteine, S-allylcysteine and S-allylmercaptocysteine or a salt thereof for use in preventing, ameliorating or treating periodontal disease.

10) One or more cysteine derivatives selected from the group consisting of S-1-propenylcysteine, S-allylcysteine and S-allylmercaptocysteine or a salt thereof for use in promoting expression of antimicrobial peptide in gingiva.

11) A method of preventing, ameliorating or treating periodontal disease, comprising administering or ingesting one or more cysteine derivatives selected from the group consisting of S-1-propenylcysteine, S-allylcysteine and S-allylmercaptocysteine or a salt thereof.

12) A method for promoting expression of antimicrobial peptide in gingiva, comprising administering or ingesting one or more cysteine derivatives selected from the group consisting of S-1-propenylcysteine, S-allylcysteine and S-allylmercaptocysteine or a salt thereof.

Advantageous Effects of Invention

According to the agent for preventing, ameliorating or treating periodontal disease according to the present invention, it is possible to slow the progression of periodontitis by eliminating periodontal bacteria in contact with the gingiva due to the effect of promoting the expression of antibacterial peptide, by staying immune cells for a long term at the inflammatory site due to the anti-inflammatory effect, and by improving gingival tissue damage and alveolar bone resorption.

DESCRIPTION OF EMBODIMENTS

Figure 1:
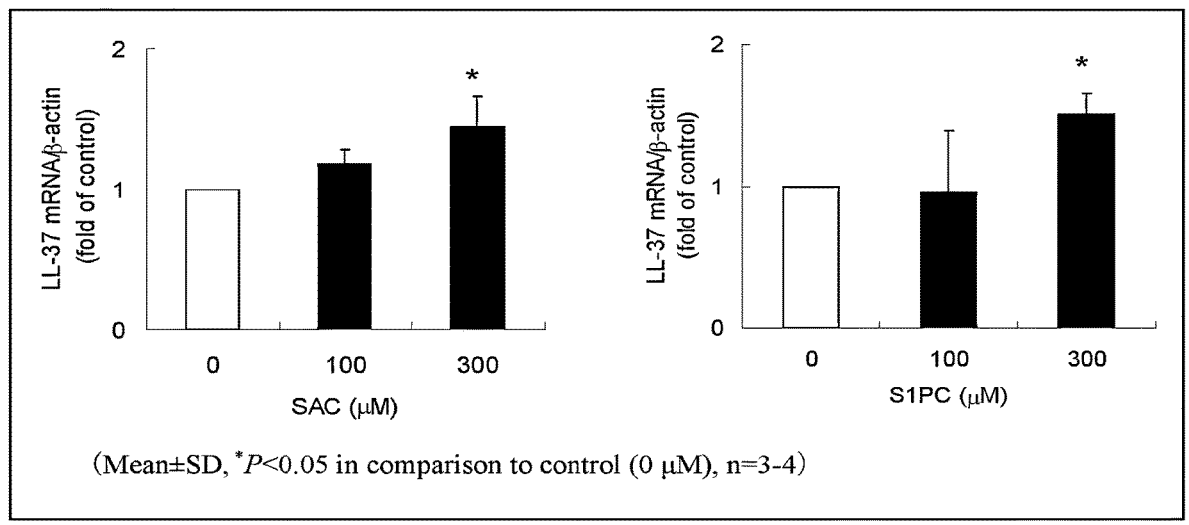
FIG. 1 illustrates a diagram showing the effect of SAC and S1PC on promoting the expression of LL-37 gene.

The cysteine derivative according to the present invention is a compound represented by formulae (1) to (3) below or a salt thereof.

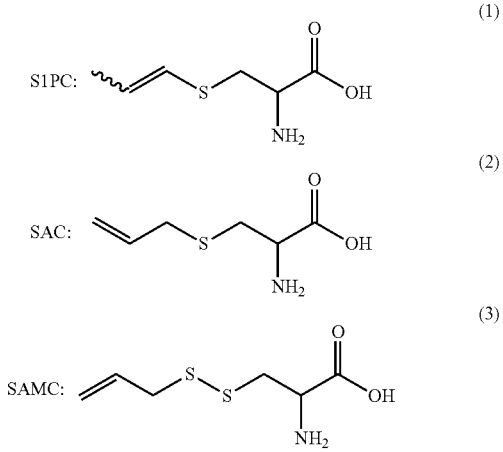

Among these, S1PC has a cis or trans configuration as indicated by a wavy line in formula (1), and the rate of the trans isomer is preferably high. When the total of the trans isomer and the cis isomer is 100%, the rate of the trans isomer preferably is from 50 to 100%, more preferably from 75 to 100%, even more preferably from 80 to 100%, and even more preferably from 90 to 100%.

The cysteine derivative according to the present invention has an asymmetric carbon derived from cysteine, and therefore an optical isomer is present and may be in any of D form, L form, or racemic form.

The salt of such cysteine derivative may be either an acid addition salt or a base addition salt. Examples of the acid addition salt include (a) salts with mineral acids such as hydrochloric acid, sulfuric acid, nitric acid, and phosphoric acid; (b) salts with organic carboxylic acids such as formic acid, acetic acid, citric acid, fumaric acid, gluconic acid, malic acid, succinic acid, tartaric acid, trichloroacetic acid, and trifluoroacetic acid; and (c) salts with sulfonic acids such as methanesulfonic acid, benzenesulfonic acid, p-toluenesulfonic acid, mesitylenesulfonic acid, and naphthalenesulfonic acid. Further, examples of the base addition salt include (a) salts with alkali metals such as sodium and potassium; (b) salts with alkaline earth metals such as calcium and magnesium; (c) ammonium salts; and (d) salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenetylamine, 1-ephenamine, and N,N'-dibenzylethylenediamine.

The cysteine derivative or a salt thereof according to the present invention can exist not only in an unsolvated form, but also in the form of hydrate or solvate. Such hydrate or solvate can exist as any crystal form depending on conditions of manufacturing. Hence, the cysteine derivative or a salt thereof in the present invention encompasses all stereoisomers, hydrates, and solvates, and encompasses all polymorphic crystal forms or amorphous forms.

The cysteine derivative or a salt thereof in the present invention can be obtained by any of organic synthetic methods [S1PC: 1] Carson J. F.; Boggs L. E. The synthesis and base-catalyzed cyslization of (+)- and (−)-cis-S-(1-propenyl)-L-cysteine sulfoxides. J. Org. Chem. 1966, 31(9), 2862-2864; 2] H Nishimura, A Mizuguchi, J Mizutani, Stereoselective synthesis of S-(trans-prop-1-enyl)-cysteine sulphoxide. Tetrahedron Letter, 1975, 37, 3201-3202; 3] J C Namyslo, C Stanitzek, A palladium-catalyzed synthesis of isoalliin, the main cysteine sulfoxide in Onion (Allium cepa). Synthesis, 2006, 20, 3367-3369; 4] S Lee, J N Kim, D H Choung, H K Lee, Facile synthesis of trans-S-1-propenyl-L-cysteine sulfoxide (isoalliin) in onions (Allium cepa). Bull. Korean Chem. Soc., 2011, 32(1), 319-320; SAC: Vesna D. Nikolic, Dusica P. Ilic, Ljubisa B. Nikolic, Mihajlo Z. Stankovic, Ljiljana P. Stanojevic, Ivan M. Savic, Ivana M. Savic, The synthesis and Structure Characterization of deoxyalliin and Alliin 1, 2012, 38-46; SAMC: Aharon Rabinkov, Talia Miron, David Mirelman, Meir Wilchek, Sabina Glozman, Ephraim Yavin, Lev Weiner, S-Allylmercaptoglutathione: the reaction product of allicin with glutathione possesses SH-modifying and antioxidant properties. Biochimica et Biophysica Acta 1499(2000) 144-153]; biochemical methods using enzymes or microbes; or methods combining these methods. In addition to these methods, the cysteine derivative or a salt thereof may be obtained by extraction and purification from plants that contain the compounds, such as an Allium plant, or processed products thereof. Hence, the cysteine derivative or a salt thereof according to the present invention may be not only an isolated and purified product, but also a crude product, or a fraction in which the content of the cysteine derivative or a salt thereof has been increased by extraction from the plants.

Here, examples of the Allium plant that contains the cysteine derivative or a salt thereof according to the present invention include garlic (Allium sativum L.), onion (Allium cepa L.), elephant garlic (Allium ampeloprasum L.), Chinese Chive (Allium tuberosum. Rottl. Ex K. Spreng.), and spring onion (Allium fistulosum L.). These plants may be used alone, or in combination. Further, the Allium plants may be used fresh as they are, or may be used after removing their outer skins if necessary, and then cutting or shredding. Alternatively, they may be powdered, or extracted by using a solvent capable of producing a medicine or food. Examples of the solvent include water, alcohol, and one obtained by adding an acid or a basic substance to a solvent.

For example, when a fraction extracted from the Allium plant is used as S1PC or a salt thereof in the present invention, the fraction may be obtained, for example, by 1) extracting the Allium plant in a 10 to 50% aqueous ethanol solution at 0 to 80° C. for one month or longer, and 2) subjecting the obtained extract to solid-liquid separation, and then collecting an ethanol elution fraction.

The aqueous ethanol solution used in step 1) may be a 10 to 50% aqueous ethanol solution, and is preferably an aqueous ethanol solution having an ethanol concentration of 20 to 40%. The treatment temperature may be set to a range from 0 to 80° C., preferably from 10 to 60° C., and more preferably from 20 to 40° C. The duration of extraction treatment under the above condition is at least one month, preferably from 1 to 20 months, and more preferably from 1 to 10 months. Taking into consideration of, for example, sanitation and volatility of ethanol, the present step may be performed in an airtight state, in a hermitically sealed state or in a closed container. It is preferred to use the closed container.

In step 2), the extract obtained in step 1) may be subjected to solid-liquid separation, and then an ethanol elution fraction is collected. The collected product is concentrated as appropriate so that an extract fraction that contains S1PC or a salt thereof can be obtained. The extract fraction may be used directly, or may be used after being appropriately dried by spray drying, for example.

Further, S1PC or a salt thereof can be isolated from the extract fraction that contains such S1PC or a salt thereof, by combining a dialysis method using a dialysis membrane with a molecular exclusion size of 3000 to 4000, if necessary, an adsorption/separation method using a cation exchange resin, and a separation/purification method based on normal phase chromatography or reverse phase chromatography.

Here, examples of the adsorption/separation method using a cation exchange resin include a method of adsorbing S1PC or a salt thereof to a cation exchange resin e.g., Amberlite (from Dow Chemical Company), DOWEX (from Dow Chemical Company), DIAION (from Mitsubishi Chemical Corporation)), and eluting it with a 0.1 to 3 N ammonia water.

Examples of the normal phase chromatography include a method of using a silica gel column and eluting it with a chloroform/methanol/water mixture.

Examples of the reverse phase chromatography include a method of using an octadecylsilyl column and eluting it with a 0.01 to 3% aqueous formic acid solution.

Preferably, there is a method including the steps of: dialyzing the above ethanol extraction fraction (dialysis membrane: molecular exclusion size=3,000 to 4,000), adsorbing the resultant to a cation exchange resin, eluting the adsorbate with a 0.5 to 2 N ammonia water, subjecting the eluate to silica gel column chromatography (solvent: a chloroform/methanol/water mixture) to collect a fraction that contains the target substance, and then further subjecting the fraction to reverse phase column chromatography for fractionation (solvent: a 0.1 to 0.5% aqueous formic acid solution) to collect the target substance.

When the total of trans isomer and cis isomer is 100°, the rate of the trans isomer in the thus obtained S1PC is more preferably 50 to 100°, even more preferably 60 to 100%, and even more preferably 70 to 100%.

Generally, the cysteine derivative or a salt thereof in the present invention has low toxicity, since, for example, the $LD_{50}$ value of a diluted ethanol extract of garlic, as one of raw materials (extracted component: 14.5%, alcohol number: 1.18) is 50 ml/Kg or higher in each of the oral, intra-abdominal, and subcutaneous administration routes (The Journal of Toxicological Sciences, 9, 57(1984)), and *Allium* plants, including garlic and onion, have been commonly used as foods.

As shown in Examples below, the cysteine derivative according to the present invention promotes the expression of antimicrobial peptide in human gingival epithelial cells that have not been stimulated with harmful components derived from periodontal pathogens, such as lipopolysaccharide (LPS). It also down-regulates the expression of ICAM-1 protein and reduces the release of IL-6 in inflammation-induced human gingival epithelial cells.

As described above, it is thought that substances that promote the production and release of antimicrobial peptide can inhibit the onset of periodontal disease (Non-Patent Literatures 4 to 6 above), and it is thought that the reduction of the release of IL-6 and the down-regulation of the expression of ICAM-1 protein can inhibit the aggravation of periodontal disease by inhibiting the differentiation of osteoclasts or inhibiting the delay of inflammatory response (Non-Patent Literatures 8 and 11 above).

Thus, the cysteine derivative or a salt thereof according to the present invention can be an agent for promoting the expression of antimicrobial peptide in the gingiva, or an agent for preventing, ameliorating or treating periodontal disease. Also, the cysteine derivative or a salt thereof according to the present invention can be used for promoting the expression of antimicrobial peptide in the gingiva, or preventing, ameliorating or treating periodontal disease.

In the present invention, the "periodontal disease" means an inflammatory disease in which inflammation is caused in the gingiva by bacteria in plaque, and includes gingivitis and periodontitis.

In the present invention, the "antimicrobial peptide" includes an antimicrobial peptide produced in oral epithelial cells, and specific examples thereof include defensins cathelicidin, LL-37 produced from cathelicidin, adrenomedullin, calprotectin, histatin and the like, but β-defensin and LL-37 are preferable.

In the present invention, the promotion of the expression of antimicrobial peptide means promoting the expression of mRNA and/or protein of the above antimicrobial peptide.

As used herein, the "preventing" means preventing or delaying the onset of a disease or condition in an individual, or reducing the risk of the onset of a disease or condition in an individual, and may be a therapeutic or non-therapeutic prevention.

The "treating" or "ameliorating" also means improving a disease, condition or state, preventing or delaying the deterioration of a disease, condition or state, or reversing, preventing or delaying the progression of a disease or condition, and the "treating" includes ameliorating a condition in addition to complete healing of a disease.

The agent for preventing, ameliorating or treating periodontal disease and the agent for promoting the expression of antimicrobial peptide in the gingiva according to the present invention may be a medicine or food which exerts an effect of preventing, ameliorating or treating periodontal disease or an effect of promoting the expression of antimicrobial peptide in the gingiva, or may be a material or a formulation which is added thereto.

The food includes food which has a concept of preventing or ameliorating periodontal disease and promoting the expression of antimicrobial peptide in the gingiva and which is labeled with the explanation of the effect based on the function as necessary, functional food, food with functional claims, food for patients, and food for specified health use.

The dosage form of a medicine that contains the cysteine derivative or a salt thereof according to the present invention is not particularly limited and may be a dosage form suitable for oral administration. Preferred dosage form is a dosage form suitable for oral administration. Specific examples of the dosage form of formulation for oral administration include solid formulations such as tablets, capsules, fine granules, pills, and granules; and liquid formulations such as emulsions, solutions, suspensions, and syrups. Such medical formulations can be prepared by appropriately combining, for example, an excipient, a binder, a disintegrant, a lubricant, a colorant, a corrigent, and a pH adjuster with the cysteine derivative or a salt thereof according to the present invention, if necessary in accordance with an ordinary method.

The form of food that contains the cysteine derivative or a salt thereof according to the present invention is not particularly limited. For example, the food may be in the various forms such as solid food, semiliquid food, gelled food, tablets, caplets, and capsules, and specifically may be in the various food forms such as sweets, beverage, seasoning agent, processed sea food, processed meat food, bread, and health food.

The food can be produced by appropriately blending food materials used to usually produce these foods with the cysteine derivative or a salt thereof according to the present invention in accordance with an ordinary method.

The medicine or food may further contain other medicinal ingredients, for example, herbal medicines such as ginseng and ginkgo, and amino acids such as glutamic acid and GABA. It may also contain vitamins, lipids, minerals, such as vitamin C, vitamin E, vitamin B2, vitamin B6, niacin, hesperidin, alpha-lipoic acid, glutathione, coenzyme Q10, zinc, magnesium and omega-3 fatty acids, which alleviate inflammation.

Daily dose of the medicine or food administered or ingested may vary depending on a subject to be administered or ingest, administration or ingestion form, types of materials and additives to be simultaneously administered or ingested, and intervals of administration or ingestion. Usually, the daily dose in terms of the cysteine derivative or a salt thereof is preferably from 0.1 to 2.7 mg/kg, and more preferably from 0.3 to 0.9 mg/kg per day. The daily dose may be divided into two to four intakes if desired.

The subject to be administered or ingest includes preferably a person who has developed gingival inflammation such as gingivitis or periodontitis, a person who desires the prevention of gingival inflammation, and the like.

EXAMPLES

Production Example 1 Production of S1PC (1)

(1) Approximately 1 kg of peeled garlic bulbs and approximately 1000 mL of 30% ethanol were placed in a container, and closed. This container was allowed to stand at room temperature for one to ten months, with appropriate stirring. The mixture was then separated into a solid and a liquid, and the liquid was concentrated by spray-drying to obtain a yellowish brown powder.

(2) The garlic ethanol extraction fraction obtained in (1) was placed in a dialysis tube with a pore size of 3,500, and dialyzed against purified water. The external dialysis solution was passed through a cation exchange resin Dowex 50Wx8 (H+), and the resin was thoroughly washed with purified water. Amino acids adsorbed to the resin were eluted with 2 N ammonia, and concentrated in vacuo. The concentrate was placed in a silica gel column, followed by column chromatography using a chloroform/methanol/water mixture as a solvent. The fractions containing a target substance (S1PC) were collected, and then concentrated. The concentrate was dissolved in water, and chromatographed on a reverse phase column for fractionation (octadecylsilyl column), using 0.1% formic acid as a solvent. The target substance was collected, and the solvent was removed by freeze-drying. The obtained freeze-dried substance was compared with the spectrum obtained from the standard substances whose structures are shown below using an NMR (solvent: deuterium oxide) and a mass spectrometer, and was confirmed to be a mixture of trans-S1PC and cis-S1PC (trans:cis=8:2)

trans-S1PC
$^1$H-NMR (500 MHz, in D2O-NaOD, δ): 1.76 (d, 3H, J=7.0 Hz), 2.98 (dd, 1H, J=7.5, 14.5 Hz), 3.14 (dd, 1H, J=4.5, 14.5 Hz), 3.69 (dd, 1H, J=4.5, 7.5 Hz), 5.10-5.14 (m, 1H), 6.02 (d, 1H, J=15.5 Hz);
$^{13}$C-NMR (125 MHz, in D$_2$O-NaOD, δ): 17.61, 33.53, 53.70, 119.92, 132.12, 172.73.
HRMS: observed [M+H]+=162.0583, calculated [M+H]+=162.0581 cis-S1PC
$^1$H-NMR (500 MHz, in D2O, δ): 1.74 (d, 3H, J=7.0 Hz), 3.21 (dd, 1H, J=7.5, 15.0 Hz), 3.31 (dd, 1H, J=4.5, 15.0 Hz), 3.95 (dd, 1H, J=4.5, 7.5 Hz), 5.82-5.86 (m, 1H), 6.01 (d, 1H, J=9.5 Hz);
$^{13}$C-NMR (125 MHz, in D$_2$O-NaOD, δ): 13.89, 33.88, 54.16, 122.58, 127.78, 172.63.
HRMS: observed [M+H]+=162.0580, calculated [M+H]+=162.0581

Production Example 2 Production of S1PC (2)

In accordance with Carson J. F.; Boggs L. E. The synthesis and base-catalyzed cyslization of (+)- and (−)-cis-S-(1-propenyl)-L-cysteine sulfoxides. Journal of Organic Chemistry 1966, 31(9), 2862-2864, S1PC was prepared with some procedures changed. That is, 2.9 g of tret-BuOK was dissolved in 100 mL of DMSO, 2.8 g of SAC was added thereto, and the mixture was stirred at room temperature overnight. After completion of reaction, 2.64 mL of concentrated hydrochloric acid was added thereto for neutralization. To this mixture, 400 mL of ethanol was added and the precipitate was collected by filtration. The precipitate was further washed with ethanol. Since the cis isomer is predominantly crystalized by recrystallization using water, the procedure of removing the crystallized cis isomer by filtration was carried out three times. After concentration of the third filtrate, the concentrate was subjected to silica gel chromatography using chloroform/methanol/water (7:3:0.5) as a solvent, and the ninhydrin-positive fraction was collected as S1PC. The structure thereof was compared with the spectrum obtained from the standard substance shown in Production Example 1 and confirmed to be a mixture of trans S1PC and cis S1PC (trans:cis=85:15).

Production Example 3 Production of SAC

In accordance with Vesna D. Nikolic, Dusica P. Ilic, Ljubisa B. Nikolic, Mihajlo Z. Stankovic, Ljiljana P. Stanojevic, Ivan M. Savic, Ivana M. Savic, THE SYNTHESIS AND STRUCTURE CHARACTERIZATION OF DEOXYALLIIN AND ALLIIN, 2012, Along 1, 38-46, SAC was prepared with some procedures changed. That is, 12.1 g of cysteine was placed in a 1,000 mL eggplant flask, and 250 mL of water was added thereto for dissolution. To this solution, 250 mL of ethanol in which 13.19 g of allyl bromide had been dissolved was added. At room temperature, 25 mL of triethylamine was added dropwise with stirring. After stirring and reacting at room temperature overnight, the mixture was concentrated and dried. The concentrate was washed with about 100 mL of ethanol, then filtered, and collected again on a filter paper. The collected product was recrystallized with 70% ethanol, and the crystals were dried in the presence of phosphorus pentaoxide in vacuo. The structure thereof was compared with the spectrum obtained from the standard substance shown below and confirmed to be the target substance.

$^1$H-NMR (in $D_2O$) δ, 2.86 (dd, J=8.2, 14.1 Hz, 1H), 3.04 (dd, J=4.8, 14.1 Hz, 1H), 3.22 (d, J=7.1 Hz, 2H), 4.56 (dd, J=4.8, 8.2 Hz, 1H), 5.19 (dd, J=9.3, 17.1 Hz, 2H), 5.80-5.88 (m, 1H);

$^{13}$C-NMR (in $D_2O$) δ, 31.6, 34.1, 52.9, 117.9, 133.7, 175.0.

Production Example 4 Production of SAMC

In accordance with Aharon Rabinkov, Talia Miron, David Mirelman, Meir Wilchek, Sabina Glozman, Ephraim Yavin, Lev Weiner, S-Allylmercaptoglutathione: the reaction product of allicin with glutathione possesses SH-modifying and antioxidant properties. Biochimica et Biophysica Acta 1499 (2000) 144-153, SAMC was prepared with some procedures changed. That is, 25 g of diallyl disulfide was dissolved in 150 mL of acetic acid and cooled in ice water. Under cooling, 22.5 g of 35% hydrogen peroxide was slowly added thereto and stirred for 6 hours for reaction to thereby prepare allicin. The reaction solution was poured into 750 mL of a water-ethanol mixture (2:1) cooled on ice, and the pH was adjusted to pH 5-6 with 28% ammonia water. Then, 27 g of cysteine hydrochloride monohydrate was dissolved in 1,000 mL of water, cooled on ice, and thereafter slowly poured into the pH adjusted allicin solution. The mixture was stirred for reaction at room temperature for 2 hours, and the precipitate was filtered and collected. The collected reaction product was washed with 1,000 mL of water twice and with 1,000 mL of ethanol twice, and dried in vacuo. The structure thereof was compared with the spectrum obtained from the standard substance shown below and confirmed to be the target substance.

$^1$H-NMR (in $D_2O$) δ, 3.00 (dd, J=9.0, 14.1 Hz, 1H), 3.27 (dd, J=4.4, 14.2 Hz, 1H), 3.38 (d, J=6.6 Hz, 2H), 4.64 (dd, J=4.4, 8.9 Hz, 1H), 5.21 (dd, J=9.2, 25.2 Hz, 1H), 5.89 (ddq, J=7.3, 10.0, 17.0 Hz, 1H);

$^{13}$C-NMR (in $D_2O$) δ, 42.0, 43.9, 56.8, 121.8, 136.5, 178.1

Test Example Effect of Inhibiting Inflammation in Gingival Cells (1) Sample Preparation Test solutions for evaluating the biological activities were prepared as follows. In evaluating the biological activities, all test solutions were prepared at the time of use.

(a) Approximately 1 mg of SAC and S1PC (cis:trans=15:85) were each precisely weighed and dissolved in 0.6 mL of purified water (10 mM). This solution was used as a stock solution and diluted appropriately to be subjected to the test.

(b) SAMC was dissolved in a culture medium for cell culture (containing 10% bovine serum albumin, 100,000 unit/mL penicillin, and 100 μg/mL streptomycin) (1 mM). This solution was used as a stock solution and diluted to be subjected to the test.

(2) Cells for Evaluation Test

Test cells (human gingival epithelial Ca9-22 cells) were purchased from the National Institute of Biomedical Innovation, Health and Nutrition. Immediately after purchasing, the culturing was initiated (5% $CO_2$, 37° C.) Subculturing was carried out two or three times per week.

(3) Enzyme-Linked Immunosorbent Assays (ELISA)

Mouse IL-6 ELISA Ready-SET-Go! Kit was purchased from eBioscience, Inc. to measure the amount of IL-6 produced. The culture supernatant was placed in a 96-well plate coated with an anti-IL-6 antibody (primary antibody). A horseradish peroxidase (HRP)-labeled secondary antibody and chromogenic substrate were added thereto and then the absorbance was measured by using a plate reader.

(4) Effect of Promoting Expression of LL-37 and hBD3 Genes

The Ca9-22 cells were prepared to $1\times10^5$ cells/mL in a 10% serum-containing medium, seeded in a 12-well plate at 1 mL respectively, and cultured for 24-48 hours. Assay was carried out when the percentage of cells in each well reached nearly 100%. In the presence or absence of heat-sterilized Porphyromonas gingivalis (HKPG), a reagent was added and the culturing was continued for 24 hours. After completion of culturing, the culture supernatant was removed and RIPA buffer (200 μL/well) was added, followed by treatment at room temperature for 5 minutes. RIPA buffer was collected from each well into tubes and chloroform was added (40 μL/tube), followed by treatment at room temperature for 2-3 minutes. After centrifugation (13,000 g, 5 min, 4° C.), the supernatant was transferred to a new tube and 2-propanol was added thereto (80 μL/tube), followed by treatment at room temperature for 10 minutes. After centrifugation (13,000 g, 10 min, 4° C.), the supernatant was removed, and 75% ethanol was added to the precipitate (200 μL/tube), and further centrifugation (13,000 g, 10 min, 4° C.) was carried out. After centrifugation (13,000 g, 10 min, 4° C.), the supernatant was removed, and the dried precipitate (total RNA) was dissolved in sterile water and cryopreserved at −80° C. until use.

Using a reverse transcription kit (PrimeScript RT reagent kit with gDNA Eraser, RR047A, TAKARA), degradation of DNA remaining in total RNA and reverse transcription reaction from RNA to complementary DNA (cDNA) were carried out. Next, cDNA derived from the target gene was amplified by quantitative real-time polymerase chain reaction (PCR) using primers specific for LL-37 or hBD3 gene. The relative expression levels of LL-37 and hBD3 genes were calculated using beta-actin as an internal reference gene. The results are shown in FIGS. 1 and 2.

Figure 2:
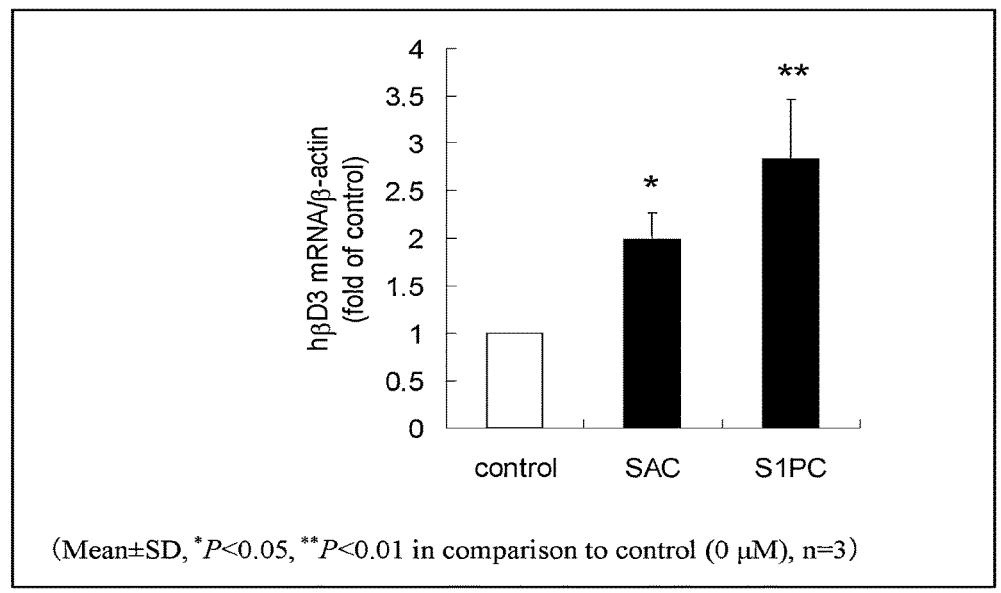
FIG. 2 illustrates a diagram showing the effect of SAC and S1PC on promoting the expression of hBD3 gene in the presence of heat-sterilized periodontal bacteria.

FIG. 1 reveals that the expression level of LL-37 gene was significantly increased by treatment with SAC or S1PC for 24 hours in the absence of HKPG, as compared to untreated ones. However, no change was observed in the expression level of hBD3 gene. On the other hand, the expression level of hBD3 gene was significantly increased by treatment with SAC or S1PC (each 300 μM) in the presence of $10^7$/mL HKPG (FIG. 2). Therefore, it is thought that the expression of hBD3 gene may be dependent on periodontal pathogens. These results suggest that SAC and S1PC may have the effect of preventing the onset of or alleviating periodontal disease through an increased expression of the antimicrobial peptides LL-37 and hBD3.

(5) Effect of Down-Regulating Expression of ICAM-1

The Ca9-22 cells were prepared to $1\times10^5$ cells/mL in a 10% serum-containing medium, seeded in a 12-well plate at 1 mL respectively, and cultured for 36-48 hours. Assay was carried out when the percentage of cells in each well reached nearly 100%. TNF-α was added to induce the expression of ICAM-1 (inflammatory response), immediately thereafter S1PC was added and culturing was continued for 24 hours. After completion of culturing, the culture supernatant was removed and the cells were washed five times with phosphate-buffered saline (PBS) cooled to 4° C. A protein extraction buffer containing several kinds of protease inhibitors was added to each well (50 μL/well), followed by treatment on ice for 30 minutes. The protein extraction buffer containing cells was collected from each well into tubes, and after centrifugation (13,000 g, 5 min, 4° C.), the supernatant was transferred to a new tube and cryopreserved at −80° C. until use.

A portion of the above protein supernatant was collected and the total protein concentration was calculated by BCA method. Subsequently, a sample buffer containing a reducing agent (dithiothreitol) and sodium dodecyl sulfate (SDS) was added thereto, heat treatment (95° C., 5 min) was carried out to denature the proteins, the denatured proteins were subjected to Western blot analysis.

In Western blot analysis, the above denatured proteins were injected at 10 μg/well into each well on the upper part of a polyacrylamide gel, then the gel was set in an electrophoresis apparatus and a voltage (150V) was applied to separate each protein based on molecular weight. The proteins in the gel were then transferred to a nitrocellulose membrane using a transfer apparatus. The protein-transferred nitrocellulose membrane was blocked in Tris-buffered saline (1% Tween20) in which 5% skim milk powder had been dissolved at room temperature for 1 hour. After blocking, the proteins on nitrocellulose membrane were washed with Tris-buffered saline three times and reacted with antibodies in rabbit anti-ICAM-1 antibody diluted into a blocking solution (1,000-fold diluted) at 4° C. overnight.

After antibody treatment, the proteins were washed with Tris-buffered saline three times and reacted with anti-ICAM-1 antibodies in HRP-labeled anti-rabbit immunoglobulin antibody diluted into a blocking solution (2,000-fold diluted) at room temperature for 1 hour. Junction treatment using HRP-labeled anti-β-actin antibody as an internal control was also carried out simultaneously. After reaction treatment, the proteins were washed with Tris-buffered saline three times, an HRP substrate was added thereto, and the luminescence intensity was detected by a luminoimage analyzer. The results are shown in FIG. 3.

Figure 3:
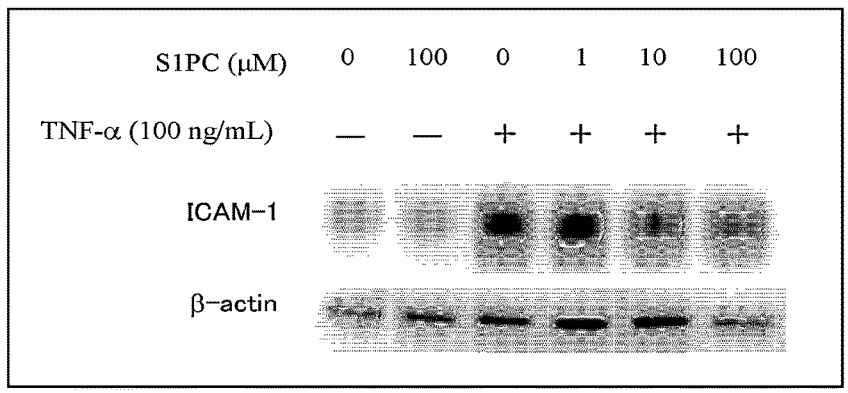
FIG. 3 illustrates a diagram showing the effect of S1PC on down-regulating the expression of ICAM-1 protein.

FIG. 3 reveals that the expression of ICAM-1 protein induced by TNF-α is concentration-dependently down-regulated by co-treatment with S1PC. Therefore, it is suggested that S1PC may control the expression of ICAM-1 in the gingival epithelial cells.

(6) Effect of Reducing Release of IL6

The Ca9-22 cells were prepared to $1 \times 10^5$ cells/mL in a 10° serum-containing medium, seeded in a 12-well plate at 1 mL respectively, and cultured for 36-48 hours. Assay was carried out when the percentage of cells in each well reached nearly 100%. TNF-α was added to induce the release of IL-6 from the Cas9-22 cells (inflammatory response), immediately thereafter SAC or SAMC was added and culturing was continued for 6 hours. After completion of culturing, the supernatant was collected and the concentration of IL-6 was measured by ELISA. The results are shown in FIGS. 4 and 5.

Figure 4:
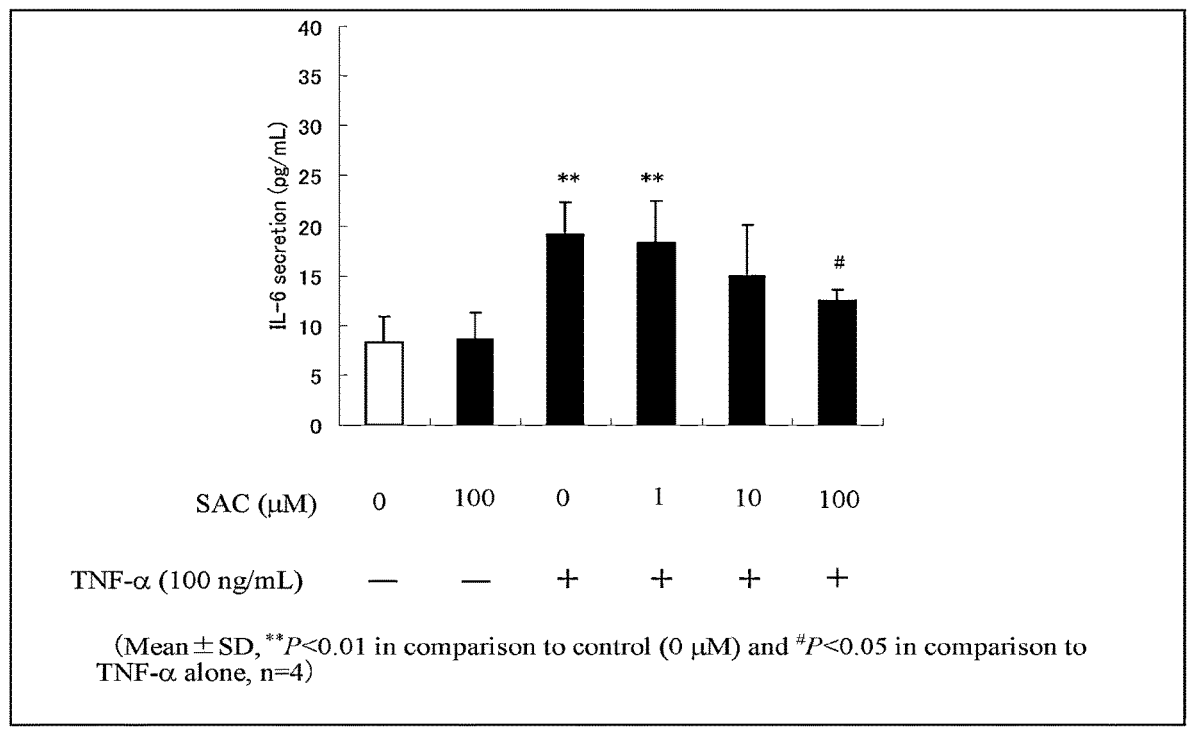
FIG. 4 illustrates a diagram showing the effect of SAC on reducing of the release of IL-6.
Figure 5:
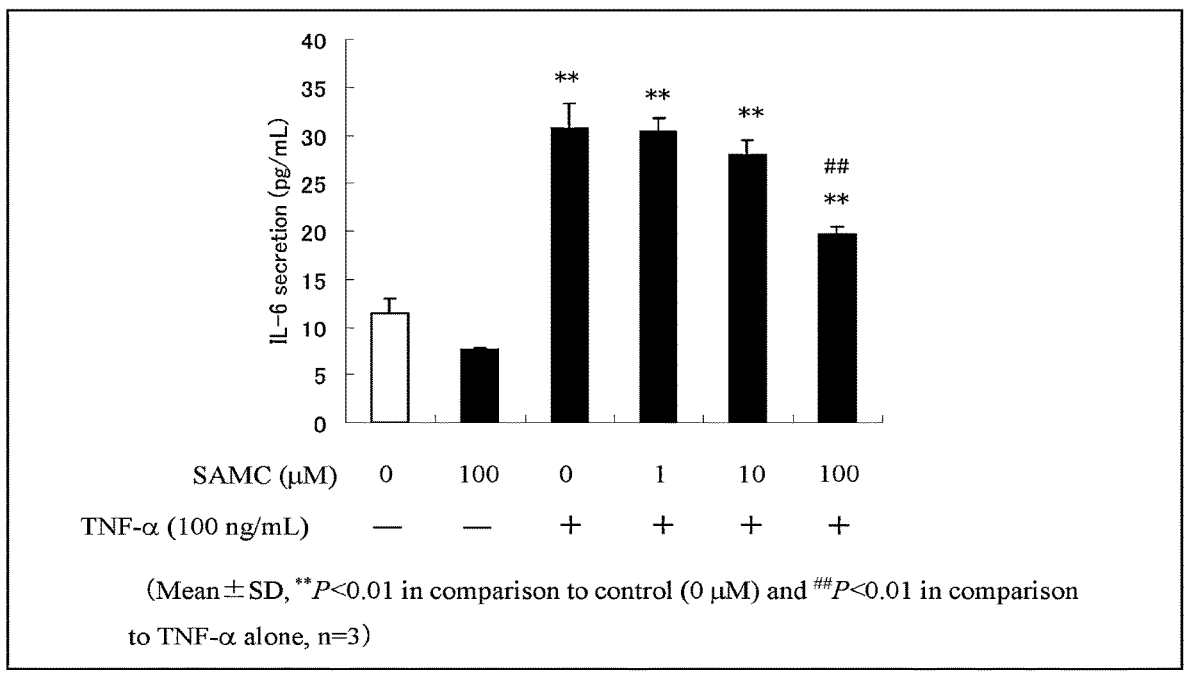
FIG. 5 illustrates a diagram showing the effect of SAMC on reducing the release of IL-6.

FIGS. 4 and 5 reveals that the amount of released IL-6 induced by TNF-α is concentration-dependently reduced by co-treatment with SAC or SAMC. Therefore, it is suggested that SAC and SAMC may control the release of IL-6 from the gingival epithelial cells.

The invention claimed is:

1. A method for preventing, ameliorating, or treating periodontal disease in a subject in need thereof, the method comprising:
   administering to or ingesting by the subject isolated S-1-propenylcysteine or a salt thereof.

2. The method of claim 1, wherein expression of an antimicrobial peptide in gingiva is promoted.

3. The method of claim 1, wherein gingival inflammation is inhibited by down-regulating expression of ICAM-1.

4. A method for preventing, ameliorating, or treating periodontal disease in a subject in need thereof, the method comprising:
   administering to or ingesting by the subject S-1-propenylcysteine or a salt thereof,
   wherein a garlic extract obtained by extracting garlic in an ethanol aqueous solution for at least one month is not administered to or ingested by the subject.

* * * * *